United States Patent
Guo et al.

(10) Patent No.: US 11,306,158 B1
(45) Date of Patent: Apr. 19, 2022

(54) METHOD FOR PREPARING HIGH-PURITY SUGAMMADEX SODIUM

(71) Applicant: HEFEI BOSIKC PHARMTECH CO., LTD., Hefei (CN)

(72) Inventors: Hui Guo, Hefei (CN); Youling Wu, Hefei (CN)

(73) Assignee: HEFEI BOSIKC PHARMTECH CO., LTD., Hefei (CN)

( * ) Notice: Subject to any disclaimer, the term of this patent is extended or adjusted under 35 U.S.C. 154(b) by 0 days.

(21) Appl. No.: 17/612,203

(22) PCT Filed: May 15, 2020

(86) PCT No.: PCT/CN2020/090535
§ 371 (c)(1),
(2) Date: Nov. 17, 2021

(87) PCT Pub. No.: WO2020/233522
PCT Pub. Date: Nov. 26, 2020

(30) Foreign Application Priority Data

May 22, 2019 (CN) .......................... 201910426525.4

(51) Int. Cl.
*C08B 37/16* (2006.01)
(52) U.S. Cl.
CPC ................ *C08B 37/0012* (2013.01)
(58) Field of Classification Search
None
See application file for complete search history.

(56) References Cited

U.S. PATENT DOCUMENTS 6,670,340 B1    12/2003   Nobel

FOREIGN PATENT DOCUMENTS

| CN | 105193863 A | 12/2015 |
| CN | 105348412 A | 2/2016 |
| CN | 106565858 A | 4/2017 |
| CN | 106749771 A | 5/2017 |
| CN | 107778383 A | 3/2018 |
| CN | 107892727 A | 4/2018 |
| CN | 109021147 A | 12/2018 |
| WO | 0140316 A1 | 6/2001 |
| WO | 2014125501 A1 | 8/2014 |

OTHER PUBLICATIONS

Julia M. Adam, et al., Cyclodextrin-Derived Host Molecules as Reversal Agents for the Neuromuscular Blocker Rocuronium Bromide: Synthesis and Structure-Activity Relationships, Journal of Medicinal Chemistry, 2002, pp. 1806-1816, vol. 45, No. 9.
Jiahu Pan, et al., Biochemical Pharmacology, 2004, pp. 103-105, 3.
Wu, Dianxing, Research and Utilization of Functional Rice, 2006, pp. 33.
Hai Ming Wang, et al., Solubilization of Polycyclic Aromatics in Water by y-Cyclodextrin Derivatives, Chem. Asian J., 2011, pp. 2390-2399, vol. 6.
Chi, Yujie, Food Additives, 2013, pp. 60.
Zhao, Xiaodan, Food Antinutritional Factors, 2015, pp. 49-52.

*Primary Examiner* — Layla D Berry
(74) *Attorney, Agent, or Firm* — Bayramoglu Law Offices LLC (57) ABSTRACT

A method for preparing high-purity sugammadex sodium, which realizes the preparation by using inositol phosphate and derivatives thereof, includes: adding a specific type of protective agent to crude sugammadex sodium, and performing recrystallization under the protection of inert gas to obtain pure sugammadex sodium. The protective agent is selected from inositol phosphate and derivatives thereof, such as inositol hexaphosphate and salts or esters thereof; one or a mixture of two or more of partial degradation products of inositol hexaphosphate, such as inositol pentaphosphate, inositol tetraphosphate, inositol triphosphate, inositol diphosphate, inositol monophosphate, and salts or esters thereof, in any ratio. The method has the advantages of simple operation, high product purity, good safety and less allergic reaction, and the method is cost-effective and more suitable for industrial production.

11 Claims, 3 Drawing Sheets

METHOD FOR PREPARING HIGH-PURITY SUGAMMADEX SODIUM

CROSS REFERENCE TO THE RELATED APPLICATIONS

This application is the national phase entry of International Application No. PCT/CN2020/090535, filed on May 15, 2020, which is based upon and claims priority to Chinese Patent Application No. 201910426525.4, filed on May 22, 2019, the entire contents of which are incorporated herein by reference.

TECHNICAL FIELD

The present invention relates to the technical field of medicine production, and in particular to a method for preparing high-purity sugammadex sodium.

BACKGROUND

The chemical name of sugammadex sodium is 6A, 6B, 6C, 6D, 6E, 7F, 6G, 6H-octa-S-(2-carboxyethyl)-6A, 6B, 6C, 6D, 6E, 7F, 6G, 6H-octathio-gamma-cyclodextrin, octa-sodium salt.

The structural formula is:

Sugammadex sodium is a novel muscle relaxant reversal agent developed by Dutch Organon Company, which is used clinically to reverse the neuromuscular blocking effect of rocuronium or vecuronium. Since the EU approved its listing in July 2008, it has been listed in Japan, South Korea, the United States and other countries, and it was listed in China in April 2018.

Sugammadex sodium is a supramolecular cyclic compound obtained by structural modification of the 6-site hydroxyl group on the gamma-cyclodextrin molecule, and its structure is complex. Since there are many active sites in the molecule and eight branches formed by substitution reaction, it is easy to produce a large number of complex by-products during the preparation process of sugammadex sodium. The thioether bond in the sugammadex sodium molecule is easily oxidized and decomposed to produce sulfoxides and thioethers. These substances are further polymerized with other impurities. The structure of the impurities is similar to that of sugammadex sodium. The polarity difference is small. The molecular weight difference is small. It is difficult to remove by a conventional means, so that it is extremely difficult to control the impurities produced in the production process.

*J. Med. Chem.* 2002, 45, 1806-1816PP proposed that in the N,N-dimethylformamide system, under the catalysis of triphenylphosphorus, bromine reacted with gamma-cyclodextrin to obtain 6-deoxy-6-perbromo-gamma-cyclodextrin. The product reacted with methyl 3-mercaptopropionate under the catalysis of anhydrous cesium carbonate to obtain the product sugammadex methyl ester, which was then hydrolyzed with sodium hydroxide to obtain sugammadex sodium. The yield was 60%. According to this method, the crude product of sugammadex sodium is obtained, the purity is low, and there is no report on further refining and purification.

Chem. Asian J. 2011, 6, 2390-2399 proposed the first iodized gamma-cyclodextrin to obtain crude 6-deoxy-6-periodo-gamma-cyclodextrin, which reacted with acetic anhydride to form an ester, which passed through a silica gel column for chromatographic purification and then was hydrolyzed with sodium methoxide to obtain refined high-purity 6-deoxy-6-periodo-gamma-cyclodextrin. Finally, an ether was formed in 3-mercaptopropionic acid to obtain the target product. The reaction intermediate has high purity and few impurities, and the post-treatment and purification of the product is relatively simple. However, the use of column chromatography to prepare iodo-gamma-cyclodextrin increases the reaction steps and takes a long time. In addition, when the iodo-gamma-cyclodextrin prepared by the method is used as a raw material to prepare sugammadex sodium, a qualified product cannot be directly obtained, and the problem that it is difficult to purify the sugammadex sodium product still exists.

WO0140316PP used iodine as a halogenating reagent to react with gamma-cyclodextrin under the catalysis of triphenylphosphorus to produce 6-deoxy-6-periodo-gamma-cyclodextrin. This intermediate and 3-mercaptopropionic acid formed a thioether, which was purified by membrane dialysis to obtain the target product. This method has a simple and reliable route, the reaction activity is high, but the purification of the product only adopts membrane dialysis, and it is more difficult to obtain high-purity sugammadex sodium.

CN105348412 disclosed a method for purifying crude sugammadex sodium. The crude sugammadex sodium was hydrolyzed under acidic conditions to obtain free acid solids. The free acid solids were pulped, washed and purified with water, and then the free acid reacted with organic amines to prepare sugammadex ammonium salt, and the obtained ammonium salt was recrystallized and purified; then freeing was performed under acidic conditions to obtain free acid, and the free acid solid was pulped, washed and purified with water, and the obtained free acid reacted with sodium hydroxide to prepare purified sugammadex sodium. This method does not use column chromatography, dialysis and other methods, but the steps are cumbersome, multiple conversions between free acid and salt are required, and it is inconvenient to operate. In addition, due to the instability of the structure of sugammadex itself, in the process of freeing under acidic conditions, its structure is at risk of dissociation, forming acid-damaging impurities and increasing the difficulty of purifying the product. This method also does not consider the protection of inert gas atmosphere, and there is no condition to inhibit the increase of oxidation impurities of sugammadex sodium.

CN107892727 disclosed a method for purifying crude sugammadex sodium. This method uses a pretreated specific type of activated carbon to remove impurities in a sugammadex sodium aqueous solution through adsorption to achieve the purpose of purifying the product. This method is low in cost, but the operation is relatively cumbersome. In addition, it has high requirements for the quality and stability of activated carbon. If the supplier changes the activated carbon production process or stops production, the process cannot be used, which limits the application of this method in pharmaceutical production.

CN107778383 disclosed a method for recrystallizing and refining sugammadex sodium, in which sulfhydryl compounds or tri-substituent organophosphorus compounds were added into sugammadex sodium to purify crude sugammadex sodium through recrystallization. This method is simple to operate and has a good impurity removal effect, but it cannot effectively remove protein residues. The used sulfhydryl compounds have a strong odor, and the residual amount in the product needs to be controlled when the tri-substituent organophosphorus compounds are used, thus increasing the application difficulty of this method.

CN106565858 disclosed a method for refining sugammadex sodium, in which sugammadex sodium was converted into a poorly water-soluble sugammadex salt by using a pretreated ion exchange resin, and then crude sugammadex sodium was further purified by means such as pulping with water. Then, ion exchange was performed by using an ion resin to convert the crude product into sugammadex sodium. This method has a better impurity removal effect, but at the same time there is a risk of introducing other metal ions into the finished sugammadex sodium.

The purification methods in the prior art have many disadvantages. Therefore, there is an urgent need for a new method for preparing high-purity sugammadex sodium to achieve effective purification to obtain pure sugammadex sodium.

SUMMARY

In order to solve the above problems, the present invention discloses a method for preparing high-purity sugammadex sodium to overcome the shortcomings in the prior art, and provides a method for recrystallizing and purifying sugammadex sodium, which has the advantages of high product purity, good safety, less allergic reaction, and high stability.

To achieve the foregoing objective, the present invention provides the following technical solutions:

A method for preparing high-purity sugammadex sodium, and a preparation process includes the following process steps:

adding a protective agent to crude sugammadex sodium, and performing recrystallization under the protection of inert gas to obtain pure sugammadex sodium. The protective agent is selected from inositol phosphate expressed by the following general formula and derivatives thereof, such as inositol hexaphosphate and salts or esters thereof; one or a mixture of two or more of partial degradation products of inositol hexaphosphate, such as inositol pentaphosphate, inositol tetraphosphate, inositol triphosphate, inositol diphosphate, inositol monophosphate, and salts or esters thereof, in any ratio. The general formula is as follows:

In the method for preparing high-purity sugammadex sodium, preferably, a mass ratio of the added protective agent to the crude sugammadex sodium is 0.001% or above, and further preferably is 0.1%-1%.

In the method for preparing high-purity sugammadex sodium, preferably, a solvent for recrystallization is selected from a combination of water and a poor solvent for sugammadex sodium. The poor solvent for sugammadex sodium is one or a mixture of more of methanol, ethanol, acetonitrile, acetone and N,N-dimethylformamide.

In the method for preparing high-purity sugammadex sodium, preferably, the preparation process includes the following specific process steps:

dissolving the crude sugammadex sodium in water, adding the protective agent, increasing the temperature under the protection of the inert gas, then adding the poor solvent for sugammadex sodium, then performing stirring to decrease the temperature to −20° C. to 30° C., and performing filtration to obtain the pure sugammadex sodium.

In the method for preparing high-purity sugammadex sodium, preferably, the inert gas is selected from one of nitrogen, argon, helium and carbon dioxide.

In natural compounds, inositol phosphate and derivatives thereof, as common biological products, have attracted the attention of the inventor.

On the one hand, compared with other kinds of antioxidants, inositol phosphate and derivatives thereof can remove free radicals and block the progress of oxidation reaction. At the same time, they are an efficient metal ion chelating agent. When applied to the present invention, it can greatly weaken the progress of sugammadex sodium oxidation reaction and inhibit the generation of oxidation impurities.

On the other hand, gamma-cyclodextrin, a starting material used in synthesis of sugammadex sodium, is produced by fermentation of starch with cyclodextrin glucosyltransferase. Protein residue in sugammadex sodium may be introduced into injection, and heterologous protein is an important cause of allergic reaction to sugammadex sodium injection.

Inositol phosphate and derivatives thereof can combine with the residual protein in sugammadex sodium to denature the residual protein to form an insoluble matter, which can be filtered and removed in the solution. This beneficial effect greatly improves the application safety of sugammadex sodium preparations.

Further, existing studies have shown that in a sterilization process of the production of sugammadex sodium injection, a color of the injection will change from colorless to yellow due to the influence of metal ions, especially iron ions, and gradually deepen, affecting the quality and stability of a final drug. By using compounds such as inositol phosphate and derivatives thereof to participate in the preparation of sugammadex sodium raw materials, the residual risk of metal ions can be reduced, and the quality and stability of the drug can be improved.

Compared with the prior art, the method has advantages in terms of purification effect, product quality, and product safety. Therefore, the application of such substances in the purification process of sugammadex sodium is of great significance.

Beneficial effects of the present invention are as follows:

1. In the process of refining sugammadex sodium by recrystallization, the protective agent inhibits the production of free radicals, and at the same time, it chelates the metal ions in the reaction system to synergistically reduce the risk of oxidation of sugammadex sodium, thus inhibiting the production of impurities and improving the purity of the sugammadex sodium product.

2. By using the method of the present invention to refine the crude sugammadex sodium, the increase of impurities can be effectively inhibited, the impurities can be removed, the purity of the product is 99.0% or above, a single impurity is not more than 0.1%, the product quality can meet the quality requirements of pharmaceutical raw materials for injections, and qualified raw materials can be provided for the production of sugammadex sodium injection.

3. The protective agent used in the present invention is selected from natural compounds with good free radical suppression effects and derivatives thereof, the source is wide, the safety and reliability are high, there is no risk such as genotoxicity, and it is more suitable for the requirements of pharmaceutical production.

4. The protective agent used in the present invention is selected from natural products with strong protein binding ability and derivatives thereof, has a very good effect on removing protein residues, especially cyclodextrin glucosyltransferase, that may exist in sugammadex sodium, can significantly reduce the risk of allergic reaction to sugammadex sodium preparations caused by heterologous proteins, and has an extremely high clinical application value.

5. The protective agent used in the present invention is selected from natural products with a good metal ion chelation effect and derivatives thereof. It has an excellent effect on reducing the metal ion residues, especially iron ion residues, in the sugammadex sodium raw materials, can significantly reduce the metal ions in the raw materials, thus can reduce the darkening of the color of the injection caused by the metal ions in the sterilization process of the sugammadex sodium preparations, and is of great significance to improve the quality and stability of the injection.

6. The refining method of the present invention has the advantages of simple process, low cost and easiness in operation, and thus is cost-effective and more suitable for industrial production; the preparations made of the raw materials have high purity, good safety and less allergic reaction, which can bring the greatest benefit to patients.

DETAILED DESCRIPTION OF THE EMBODIMENTS

More detailed descriptions of exemplary implementations of the method of the present invention are provided below. It should be correctly understood that the method in the embodiments of the present invention is merely used for further describing the present invention, but is not intended to limit the present invention, Therefore, all simple improvements made to the present invention based on the method of the present invention shall fall within the protection scope of the present invention.

Unless otherwise stated in the present invention, the reagents, instruments and equipment used are all commercially available products.

Crude sugammadex sodium is produced with reference to the method disclosed in U.S. Pat. No. 6,670,340.

Reference Embodiment

Figure 1:
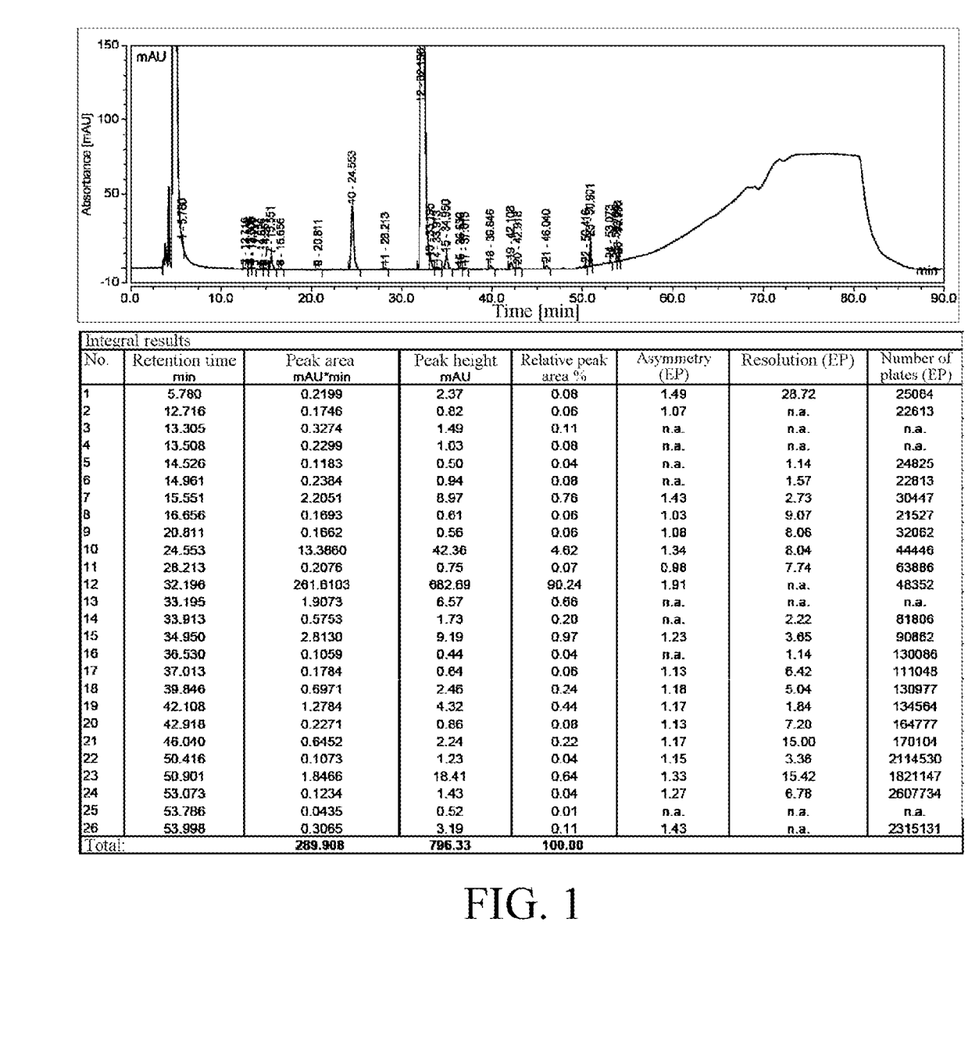
FIG. 1 illustrates an HPLC pattern of crude sugammadex sodium according to the present invention.

Preparation of Crude Sugammadex Sodium 3-mercaptopropionic acid (12.2 mL, 140 mol) was put into a reaction flask, 450 mL of N,N-dimethylformamide was added, sodium hydride (12.3 g, 308 mol, 60%) was added in three batches under the protection of nitrogen at room temperature. Then stirring was performed for 30 minutes at room temperature, gamma-iodocyclodextrin (31.2 g, 14 mmol, dissolved in 450 mL of N,N-dimethylformamide) was dropped, and then the temperature was increased to 70° C. for reaction for 12 h. After the reaction was completed, cooling to room temperature was performed, 100 mL of water were added, stirring was performed, and reduced pressure distillation was performed until the amount of a remaining solvent was 400 mL, 2 L of ethanol was added, filtration was performed, a solid was collected, and vacuum drying was performed to obtain 45 g of off-white solid with a purity of 91.92%. Test results of crude sugammadex sodium were as shown in FIG. 1.

Sterilization Color Investigation Test of Sugammadex Sodium Injection:

1 g of sugammadex sodium sample was taken, filled with nitrogen for protection, and then dissolved in 8 ml of water for injection, heating was performed for dissolution, the pH value was regulated, and water for injection was added to fix the volume to 10 ml. The above liquid was enabled to pass through a 0.22 m filter membrane and then was filled into a vial, a rubber stopper was added for capping, and the vial was placed in a sterilizer for sterilization at 121° C. for 30 min. Whether the color was changed was checked.

Sugammadex Sodium Protein Residue Detection Test (Coomassie Brilliant Blue G-250 Method):

0, 6, 12, 24, 36, 48 and 60 μl of standard protein solution were respectively added to test tubes, 3 ml of Coomassie Brilliant Blue G-250 staining solution was added, uniform mixing was performed, heat preservation was performed at room temperature for 15 min, colorimetric determination was performed at wavelength of 595 nm. and a standard curve was drawn.

1 g of sugammadex sodium sample to be tested was taken and dissolved in 8 ml of water for injection, heating was performed for dissolution, the pH value was regulated, water for injection was added to fix the volume to 10 ml, the above liquid was enabled to pass through a 0.22 μm filter membrane, and then a sample solution to be tested was prepared. 60 μl of the solution was taken and the above determination was performed to obtain the concentration thereof.

Figure 2:
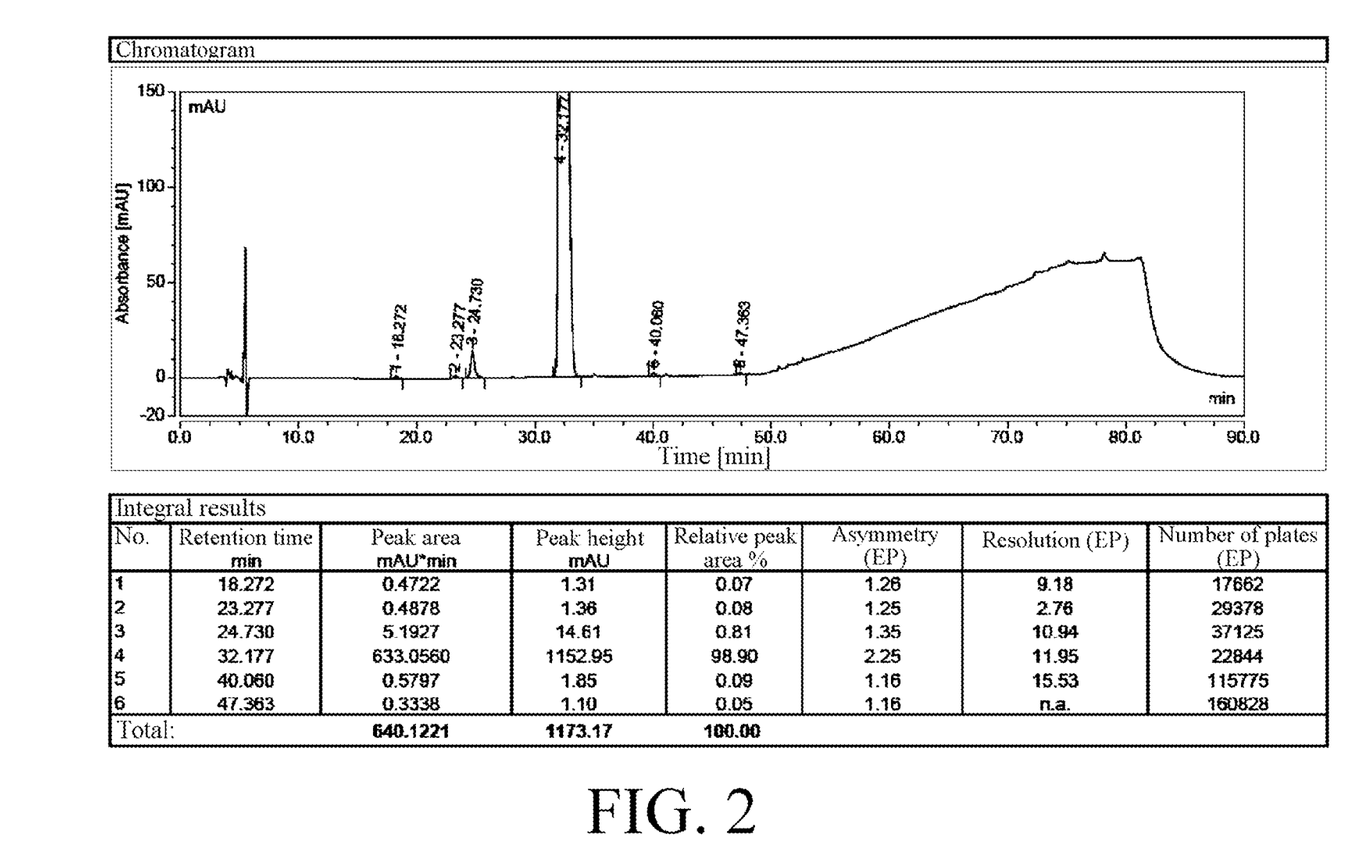
FIG. 2 illustrates an HPLC pattern of pure sugammadex sodium obtained by adopting a method according to the present invention.

Embodiment 1: Refining of Sugammadex Sodium 100.0 g of crude sugammadex sodium was taken and dissolved with 0.3 L of water until it was clear, 2.0 g of inositol hexaphosphate (50% aqueous solution) was added under stirring, the temperature was increased to 80° C. under the protection of nitrogen, 0.8 L of N,N-dimethylformamide was added to the solution, then stirring was performed to decrease the temperature to room temperature, a large amount of white solid was precipitated, and suction filtration was performed to obtain 39.8 g of pure sugammadex sodium with a purity of 99.8%, as shown in FIG. 2.

Of course, stirring may also be performed to decrease the temperature to −20° C. to 30° C.

Embodiment 2: Refining of Sugammadex Sodium 100 g of crude sugammadex sodium was taken and dissolved with 1 L of water until it was clear, 1 g of inositol diphosphate was added under stirring, the temperature was increased to 70° C. under the protection of nitrogen, and 6 L of acetonitrile was added to the solution. Then, stirring was performed to decrease the temperature to room temperature, a large amount of white solid was precipitated, and suction filtration was performed to obtain 32.3 g of pure sugammadex sodium with a purity of 99.5%.

The protective gas may also be selected from one of nitrogen, argon, helium, and carbon dioxide.

Embodiment 3: Refining of Sugammadex Sodium 100 g of crude sugammadex sodium was taken and dissolved with 0.5 L of water until it was clear, 3 g of inositol monophosphate was added under stirring, the temperature was increased to reflux under the protection of nitrogen, and 2 L of ethanol was added to the solution. Then, stirring was performed to decrease the temperature to room temperature, a large amount of white solid was precipitated, and suction filtration was performed to obtain 29.9 g of pure sugammadex sodium with a purity of 99.6%.

Embodiment 4: Refining of Sugammadex Sodium 100 g of crude sugammadex sodium was taken and dissolved with 0.3 L of water until it was clear, 0.5 g of inositol triphosphate was added under stirring, the temperature was increased to 60° C. under the protection of nitrogen, and 2 L of acetone was added to the solution. Then, stirring was performed to decrease the temperature to room temperature, a large amount of white solid was precipitated, and suction filtration was performed to obtain 32.1 g of pure sugammadex sodium with a purity of 99.7%.

Embodiment 5: Refining of Sugammadex Sodium 100 g of crude sugammadex sodium was taken and dissolved with 0.3 L of water until it was clear, 0.8 g of inositol tetraphosphate was added under stirring, the temperature was increased to 80° C. under the protection of nitrogen, and 1 L of N,N-dimethylformamide was added to the solution. Then, stirring was performed to decrease the temperature to room temperature, a large amount of white solid was precipitated, and suction filtration was performed to obtain 37.2 g of pure sugammadex sodium with a purity of 99.7%.

Embodiment 6: Refining of Sugammadex Sodium 100 g of crude sugammadex sodium was taken and dissolved with 3 L of water until it was clear, 0.2 g of inositol pentaphosphate was added under stirring, the temperature was increased to 70° C. under the protection of nitrogen, and 8 L of acetonitrile was added to the solution. Then, stirring was performed to decrease the temperature to room temperature, a large amount of white solid was precipitated, and suction filtration was performed to obtain 34.7 g of pure sugammadex sodium with a purity of 99.6%.

Embodiment 7: Refining of Sugammadex Sodium 100 g of crude sugammadex sodium was taken and dissolved with 0.3 L of water until it was clear, 0.8 g of CPPM (CAS No. 2271351-38-1, 1,2,3,4,5-Cyclohexanepentol,6-[(phosphonooxy)methyl]) was added under stirring, the temperature was increased to 80° C. under the protection of nitrogen, and 1 L of N,N-dimethylformamide was added to the solution. Then, stirring was performed to decrease the temperature to room temperature, a large amount of white solid was precipitated, and suction filtration was performed to obtain 36.1 g of pure sugammadex sodium with a purity of 99.7%.

Embodiment 8: Refining of Sugammadex Sodium 100 g of crude sugammadex sodium was taken and dissolved with 0.3 L of water until it was clear, 0.9 g of L-CIPM (CAS No. 1313195-32-2, L-chiro-Inositol,2,3-dideoxy-3-[(phosphonooxy)methyl]) was added under stirring, the temperature was increased to 80° C. under the protection of nitrogen, and 1 L of N,N-dimethylformamide was added to the solution. Then, stirring was performed to decrease the temperature to room temperature, a large amount of white solid was precipitated, and suction filtration was performed to obtain 37.5 g of pure sugammadex sodium with a purity of 99.6%.

Embodiment 9: Refining of Sugammadex Sodium 100 g of crude sugammadex sodium was taken and dissolved with 0.3 L of water until it was clear, 0.8 g of CDPM (CAS No. 127233-15-2, 1,2-Cyclohexanediol,4-[(phosphonooxy)methyl],bis(dihydrogen phosphate)) was added under stirring, the temperature was increased to 80° C. under the protection of nitrogen, and 1 L of N,N-dimethylformamide was added to the solution. Then, stirring was performed to decrease the temperature to room temperature, a large amount of white solid was precipitated, and suction filtration was performed to obtain 38.3 g of pure sugammadex sodium with a purity of 99.8%.

Embodiment 10: Sterilization Color Investigation of Sugammadex Sodium Injection 1 g of the sugammadex sodium product prepared in Embodiments 1-9 was taken respectively, filled with nitrogen for protection, and then dissolved in 8 ml of water for injection, heating was performed for dissolution, the pH value was regulated, and water for injection was added to fix the volume to 10 ml. The above liquid was enabled to pass through a 0.22 m filter membrane and then was filled into a vial, and a rubber stopper was added for capping. The vial was placed in a sterilizer for sterilization at 121° C. for 30 min. It was detected that the sample was colorless and transparent. Compared with the sample before sterilization, the color was not darkened. Compared with the commercially available injections, the color was obviously lighter.

Embodiment 11

100.0 g of crude sugammadex sodium was taken, added with 0.1% cyclodextrin glucosyltransferase and dissolved with 0.3 L of water until it was clear, 2.0 g of inositol hexaphosphate (50% aqueous solution) was added under stirring, the temperature was increased to 80° C. under the protection of nitrogen, 0.8 L of N,N-dimethylformamide was added to the solution, then stirring was performed to decrease the temperature to room temperature, a large amount of white solid was precipitated, and suction filtration was performed to obtain 39.3 g of pure sugammadex sodium. The sample was detected by the above protein residue detection method (Coomassie Brilliant Blue G-250 Method), and no protein residue was detected.

Comparative Embodiment 1

Figure 3:
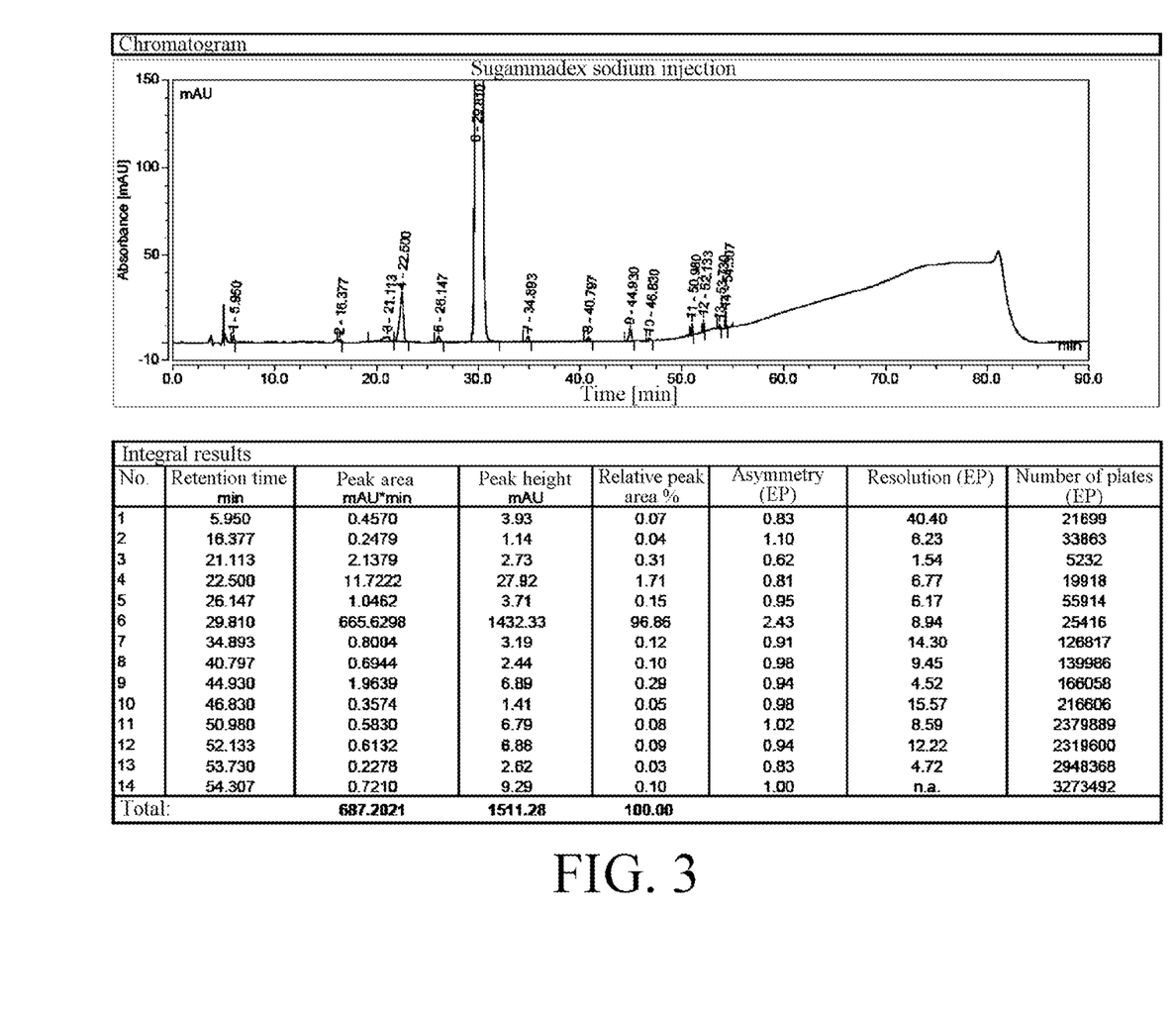
FIG. 3 illustrates an HPLC pattern of a commercially available sugammadex sodium injection.

The purity of a sugammadex sodium injection produced by a commercial original research manufacturer was 98.56% (FIG. 3).

Comparing Comparative Embodiment 1 with Embodiments 1-9, it can be seen that the pure sugammadex sodium obtained in the present invention has higher purity than the commercially available products, and the number of impurities is far less than that of the commercially available preparations.

Comparative Embodiment 2: Comparison of Ability of Protective Agent to Remove Residual Protein 100 g of crude sugammadex sodium was taken, added with 0.1% cyclodextrin glucosyltransferase and dissolved with 0.3 L of water, the temperature was increased to 80° C. under the protection of nitrogen, 0.8 L of N,N-dimethylformamide was added to the solution, then stirring was performed to decrease the temperature room temperature, a large amount of white solid was precipitated, and filtration was performed to obtain 37.1 g of pure sugammadex sodium. The sample was detected by the above protein residue detection method (Coomassie Brilliant Blue G-250 Method), and the content of protein was 0.06 μg/ml.

The technical means disclosed in the solutions of the present invention are not limited to the technical means disclosed in the foregoing implementations, and also includes technical solutions including any combination of the foregoing technical features. It should be noted that a person of ordinary skill in the art may make several improvements and modifications without departing from the principle of the present invention, and such modifications and modifications shall fall within the protection scope of the present invention.

What is claimed is:

1. A method for preparing high-purity sugammadex sodium, comprising:
adding a protective agent to crude sugammadex sodium, and performing a recrystallization under a protection of inert gas to obtain pure sugammadex sodium, wherein the protective agent is selected from inositol phosphate expressed by the following general formula and derivatives thereof:

2. The method for preparing the high-purity sugammadex sodium according to claim 1, wherein the inositol phosphate and the derivatives thereof are inositol hexaphosphate and salts or esters thereof; or one or a mixture of two or more of partial degradation products of the inositol hexaphosphate, comprising inositol pentaphosphate, inositol tetraphosphate, inositol triphosphate, inositol diphosphate, inositol monophosphate, and salts or esters thereof, in any ratio.

3. The method for preparing the high-purity sugammadex sodium according to claim 1, wherein a mass ratio of the protective agent to the crude sugammadex sodium is 0.001% or above.

4. The method for preparing the high-purity sugammadex sodium according to claim 3, wherein the mass ratio of the protective agent to the crude sugammadex sodium is 0.1%-1%.

5. The method for preparing the high-purity sugammadex sodium according to claim 1, wherein a solvent for the recrystallization is selected from a combination of water and a poor solvent for sugammadex sodium.

6. The method for preparing the high-purity sugammadex sodium according to claim 5, wherein the solvent for the recrystallization is selected from the combination of water and the poor solvent for sugammadex sodium, and the poor solvent for sugammadex sodium is one solvent or a mixture of more than one solvent selected from the group consisting of methanol, ethanol, acetonitrile, acetone, and N,N-dimethylformamide.

7. The method for preparing the high-purity sugammadex sodium according to claim 6, wherein the method comprises the following specific process steps: dissolving the crude sugammadex sodium in water, adding the protective agent, increasing a temperature under the protection of the inert gas, then adding the poor solvent for sugammadex sodium, then performing stirring to decrease the temperature to −20° C. to 30° C., and performing a filtration to obtain the pure sugammadex sodium.

8. The method for preparing the high-purity sugammadex sodium according to claim 1, wherein the inert gas is selected from the group consisting of nitrogen, argon, helium, and carbon dioxide.

9. The method for preparing the high-purity sugammadex sodium according to claim 2, wherein a solvent for the recrystallization is selected from a combination of water and a poor solvent for sugammadex sodium, and the poor solvent for sugammadex sodium is one solvent or a mixture of more than one solvent selected from the group consisting of methanol, ethanol, acetonitrile, acetone, and N,N-dimethylformamide.

10. The method for preparing the high-purity sugammadex sodium according to claim 3, wherein a solvent for the recrystallization is selected from a combination of water and a poor solvent for sugammadex sodium, and the poor solvent for sugammadex sodium is one solvent or a mixture of more than one solvent selected from the group consisting of methanol, ethanol, acetonitrile, acetone, and N,N-dimethylformamide.

11. The method for preparing the high-purity sugammadex sodium according to claim 4, wherein a solvent for the recrystallization is selected from a combination of water and a poor solvent for sugammadex sodium, and the poor solvent for sugammadex sodium is one solvent or a mixture of more than one solvent selected from the group consisting of methanol, ethanol, acetonitrile, acetone, and N,N-dimethylformamide.

* * * * *